US010660591B2

(12) United States Patent
Kraemer et al.

(10) Patent No.: US 10,660,591 B2
(45) Date of Patent: May 26, 2020

(54) EXAMINATION OR TREATMENT FACILITY COMPRISING A C-ARM

(71) Applicant: Siemens Healthcare GmbH, Erlangen (DE)

(72) Inventors: Alexander Kraemer, Irchenreith (DE); Michael Meyer, Hausen (DE); Martin Seifert, Bayreuth (DE)

(73) Assignee: Siemens Healthcare GmbH, Erlangen (DE)

(*) Notice: Subject to any disclaimer, the term of this patent is extended or adjusted under 35 U.S.C. 154(b) by 92 days.

(21) Appl. No.: 15/980,792

(22) Filed: May 16, 2018

(65) Prior Publication Data

US 2018/0333115 A1    Nov. 22, 2018

(30) Foreign Application Priority Data

May 19, 2017 (DE) .................. 10 2017 208 557

(51) Int. Cl.
*A61B 6/00* (2006.01)
(52) U.S. Cl.
CPC .......... *A61B 6/4441* (2013.01); *A61B 6/4405* (2013.01); *A61B 6/4423* (2013.01); *A61B 6/461* (2013.01)
(58) Field of Classification Search
CPC ........ A61B 6/4441; A61B 2017/00951; A61B 2050/21; A61B 50/20; A61B 6/4405; A61B 6/461; A61B 6/5258; A61B 6/587
See application file for complete search history.

(56) References Cited

U.S. PATENT DOCUMENTS

| 6,132,087 A | 10/2000 | Kusch et al. |
| 10,105,149 B2* | 10/2018 | Haider ............... A61B 17/17 |
| 2005/0047734 A1 | 3/2005 | Borom |
| 2007/0280426 A1 | 12/2007 | Saffer |
| 2017/0119324 A1* | 5/2017 | Wilson ............... A61B 6/107 |

FOREIGN PATENT DOCUMENTS

| DE | 19746079 A1 | 4/1999 |
| DE | 102004011460 A1 | 10/2005 |

OTHER PUBLICATIONS

German Office Action #102017208557.6 dated Nov. 15, 2017.

* cited by examiner

*Primary Examiner* — David P Porta
*Assistant Examiner* — Fani Boosalis
(74) *Attorney, Agent, or Firm* — Harness, Dickey & Pierce, P.L.C.

(57) ABSTRACT

An examination or treatment facility includes a C-arm, movable along a circular path relative to a bracket supporting the arm. In an embodiment, the C-arm includes a bent carrier with a U-shaped cross-section, movable on a guidance facility provided on the bracket. The carrier is accommodated in a covering part with a C-shaped cross-section. The covering part includes its open side directed toward the guidance facility and is closed via flexible sealing elements, movable apart by the guidance facility.

20 Claims, 4 Drawing Sheets

EXAMINATION OR TREATMENT FACILITY COMPRISING A C-ARM

PRIORITY STATEMENT

The present application hereby claims priority under 35 U.S.C. § 119 to German patent application number DE 102017208557.6 filed May 19, 2017, the entire contents of which are hereby incorporated herein by reference.

FIELD

At least one embodiment of the invention generally relates to an examination or treatment facility comprising a C-arm, movable along a circular path relative to a bracket supporting the arm.

BACKGROUND

Examination or treatment facilities of this kind are mostly embodied as imaging systems, for example as x-ray facilities comprising a radiation source and a radiation receiver, which are arranged opposite one another on the C-arm. They are used in various different fields of application, for example in the field of angiography.

As part of the imaging, in systems of this kind the C-arm moves around an isocenter; it is moved along a circular path. To this end, it is guided in a bracket which has a fixed position relative to the arm, but in turn is often rotatable, in order to be able to adapt the spatial alignment of the arm etc. To move the arm, there is provision for a corresponding drive, usually comprising an exposed drive belt which runs on the outside of the C-arm and which is guided via a corresponding, bracket-side drive pinion. To guide the arm on the bracket, there is frequently provision for an exposed guidance system comprising bracket-side rollers and arm-side running wires, on which the rollers roll. Power is supplied to the operating components arranged on the C-arm by cables or supply lines accommodated in external guides along the C-arm.

To avoid any infections which could be picked up in the course of such an examination, a good cleanability of the equipment used is advantageous. This is not always the case, however, in known examination or treatment facilities, in particular in the region of the guide and drive of the C-arm, as the running wires and rollers for example are partially difficult to access and can only be cleaned with considerable effort—the same applies in relation to the belt drive.

A medical facility with a support apparatus is known in DE 197 46 079 A1, which can be adjusted relative to a retaining apparatus and is made of plastic, in the form of a C-arm. The C-arm is guided on rollers on the retaining apparatus. It has a hollow, closed base part, to which two add-on parts facing one another and curved in a C-shape are fastened. By way of these parts, recesses are delimited, in which the rollers run during the adjustment of the C-arm relative to the retaining apparatus on the C-arm.

Also known in U.S. Pat. No. 7,108,422 B2 is a medical facility with a C-arm guided such that it can move along a bracket. The C-arm is surrounded by a sterile enclosure, which can be closed around the C-arm via a suitable sealing material.

Finally, a C-arm device is known from DE 10 2004 011 460 A1 with a C-arm which can move along a bracket, wherein here too the C-arm has an approximately semicircular hollow profile, which on the side facing toward the bracket has a corresponding recess or socket, into which the corresponding rollers of the movement apparatus engage.

SUMMARY

The inventors have recognized that a problem underlying at least one embodiment of the invention is thus to specify an examination or treatment facility which is improved in comparison.

According to at least one embodiment of the invention there is provision in the case of an examination or treatment facility of the type mentioned in the introduction for the C-arm to comprise a bent carrier with a U-shaped cross-section, which is guided such that it can move on a guidance facility provided on the bracket, wherein the carrier is accommodated in a covering part with a C-shaped cross-section, which covering part has its open side directed toward the guidance facility and is closed via flexible sealing elements, which can be moved apart by the guidance facility.

BRIEF DESCRIPTION OF THE DRAWINGS

Further advantages and details of the present invention are disclosed in the following description of example embodiments and by reference to the drawings, in which.

DETAILED DESCRIPTION OF THE EXAMPLE EMBODIMENTS

Figure 1:
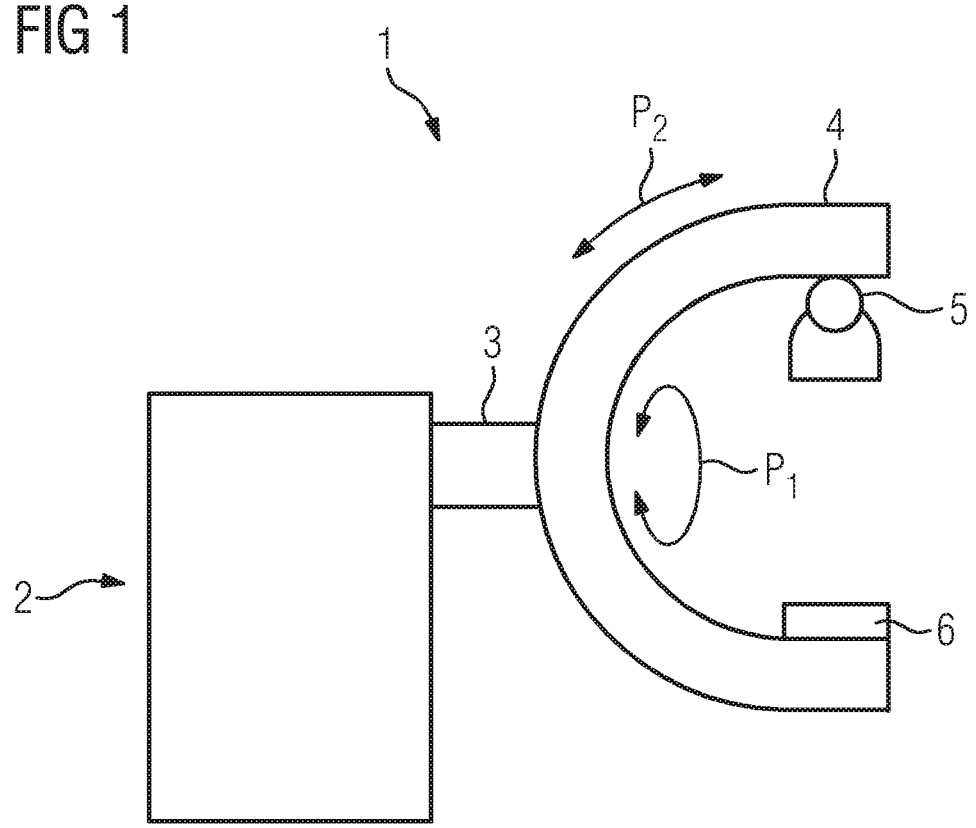
FIG. 1 shows a schematic representation of an examination or treatment facility according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to at least one embodiment of the invention there is provision in the case of an examination or treatment facility of the type mentioned in the introduction for the C-arm to comprise a bent carrier with a U-shaped cross-section, which is guided such that it can move on a guidance facility provided on the bracket, wherein the carrier is accommodated in a covering part with a C-shaped cross-section, which covering part has its open side directed toward the guidance facility and is closed via flexible sealing elements, which can be moved apart by the guidance facility.

The C-arm is characterized on the one hand by a carrier with a U-shaped cross-section, the open side of which is directed toward the guidance facility, that is to say it can engage into the carrier. According to at least one embodiment of the invention, the carrier itself is completely enclosed. This takes place on the one hand via a covering part with a C-shaped cross-section, which is arranged on the inside of the arm and extends up to the outside of the arm. In this region, there is provision on the covering part for flexible sealing elements directed toward one another, which preferably abut one another and close off the U-shaped carrier open toward this side.

Since, as described, the carrier can be moved along the fixed-position bracket or guidance facility, respectively, it is necessary for the sealing elements to be guided past the guidance facility. This is readily possible, since the sealing elements are flexible and can be moved apart by the guidance facility. If the C-arm is thus moved from a first position along the circular path, then it slides along the guidance facility, which opens the flexible sealing elements running towards it, wherein the sealing elements immediately close again if they are moved past the guidance facility. This ultimately means that the carrier is completely closed and enclosed at all times. The covering part and the sealing elements can be cleaned very easily and are accessible without problems, so that the problems mentioned in the introduction are no longer present in the facility according to at least one embodiment of the invention.

Furthermore, the embodiment according to the invention also offers the possibility of constructing the guide and drive elements in particular such that they are likewise encapsulated or covered, respectively. Depending on whether a linear guide or a belt drive is used, the corresponding components can be arranged and guided in the interior of the U-shaped carrier, i.e. covered by the covering part or the sealing elements, respectively, wherein the drive is on the bracket. The guidance facility itself, for example a roller or plain bearing, can likewise be arranged inside the carrier, so that these components are also no longer exposed. Overall, this results in a completely encapsulated, enclosed arm, which has large surfaces without edges and gaps and is thus designed in a hygiene-friendly manner and has a very good level of cleanability.

The covering part itself can either have an elliptical or a round C-shaped cross-section. This primarily serves the covering alone, not the accommodation of any components or the like, as these are preferably accommodated in the interior of the carrier.

A central feature according to at least one embodiment of the invention are the flexible sealing elements. Depending on how far the covering part moves around or how wide the guidance facility is in the region between the sealing elements, respectively, these sealing elements have to span a certain distance between the fastening on the covering part or the carrier and the opposite contact level. Therefore, flexible sealing strips, which run along the open side and preferably abut one another, are preferably used as sealing elements. These have a sufficient width to make it possible to span the corresponding distance.

To avoid dirt penetrating into the interior of the carrier or the covering part, respectively, the sealing elements preferably abut one another. In order to ensure that there is a sufficiently fixed contact, a particularly expedient development of the invention provides that the sealing elements, in particular the sealing strips, stick together magnetically in the region of their abutting ends. The sealing elements are thus provided with corresponding magnet elements in the region of their abutting ends, so that they stick together at their ends via a magnetic, yet releasable, coupling. It is hereby ensured that the sealing elements are interconnected and abut in any position.

As an alternative to the magnetic coupling, it is conceivable that the sealing elements, in particular the sealing strips, can be releasably interconnected in the manner of a zipper. According to this embodiment of the invention, the ends of the abutting sealing elements or sealing strips, respectively, are provided with corresponding zipper-like geometries, which are able to be interconnected in a semi-mechanical manner. The zipper connection can be opened by the guidance facility when moving past the C-arm, but can equally be closed again at the other end of the guidance facility. This also means that a sufficiently stable, secure connection can be ensured.

As described, the sealing elements or sealing strips, respectively, are moved apart by the guidance facility—if they have passed the guidance facility, they converge again, which takes place in effect automatically due to their flexibility or the resetting force generated when they are moved apart, respectively. For simple opening of the sealing elements, it is expedient if the guidance facility is embodied as tapering off in the front and rear region in contact with the sealing elements. This means that the guidance facility, which is in any case embodied as narrow and elongated as possible, has a tapered or wedge shape in the region of the front and rear end, i.e. the regions which are in contact with the sealing elements, so that the sealing elements can be gently guided apart and together.

It is expedient if one or more cables or lines are guided inside the U-shaped carrier. As already described, the components constructed on the arm-side are to be supplied accordingly. According to at least one embodiment of the invention, it is now possible to accommodate the cables or lines inside the U-shaped carrier and guide them to the components, so that these too are no longer exposed, but rather encapsulated. Feeding the lines or cables can also take place via the bracket, meaning that they arrive in the carrier in the region of the guidance facility. This means that no external components, with the exception of the specific add-on components, are provided on the C-arm or there are no exposed components which would in principle impede the cleanability.

For reasons of stability, it can be expedient if a stabilization carrier arranged inside the covering part and connected to the carrier is provided as a reinforcement component. This preferably runs on the inner side of the carrier and is thus likewise captured by the covering part and encapsulated thereby.

The stabilization carrier is preferably a rectangular hollow profile, but it can also have another geometric cross-sectional shape.

FIG. 1 shows a schematic representation of an examination or treatment facility 1 according to an embodiment of the invention, comprising a facility frame 2, which can also be embodied as a frame, on which a corresponding bracket 3 is arranged, which in turn supports a C-arm 4. Arranged on the C-arm 4 in the example shown are a radiation source 5 and a radiation detector 6.

On the one hand, the C-arm 4 can be rotated about the longitudinal axis of the bracket 3, as shown by the double arrow P1. In particular, however, it can be moved along the bracket 3 on a circular path, as shown by the arrow P2. This means that it can be displaced on the circular path via a corresponding drive facility relative to the bracket 3. The basic structure of such an examination or treatment facility, for example an angiography apparatus, is known.

Figure 2:
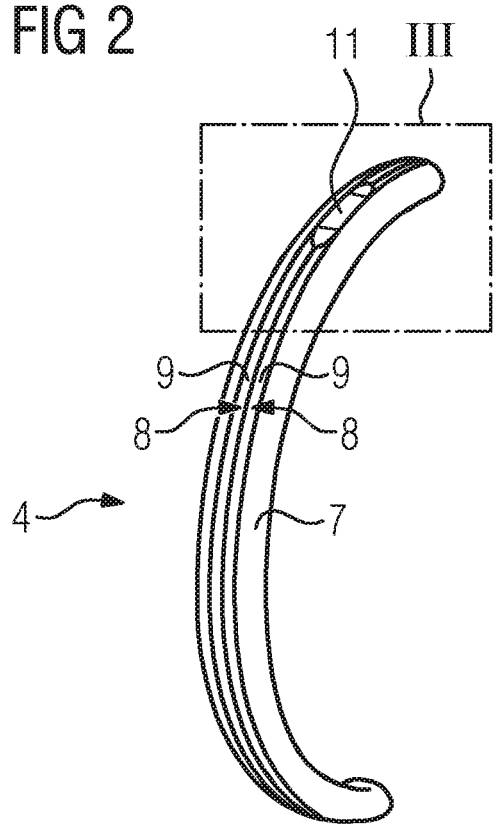
FIG. 2 shows an enlarged partial view of the C-arm with covering parts and flexible sealing elements.
Figure 3:
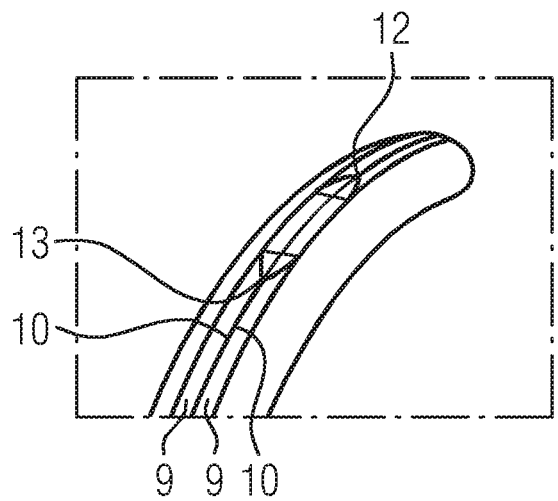
FIG. 3 shows an enlarged partial view of the region III from FIG. 2.

FIG. 2 shows an enlarged partial view of the C-arm 4 in a perspective representation, while FIG. 3 shows an enlarged partial view of the region III. The C-arm 4 comprises, in addition to a carrier along with stabilization carrier provided in the interior (not shown in more detail here), an outer covering part 7 with a C-shaped cross-section, preferably made of plastic, which is positioned on the inner side of the C-arm and extends toward the outer side. Arranged on the outer side are two sealing elements 8 fastened to the covering part 7, in which the sealing elements 8 involve flexible sealing strips 9 made of a plastics material, wherein the sealing strips 9 abut one another closely. For this purpose magnet elements 10 can be integrated in the region of the abutting contact edges 10, so that a magnetic closure results. Alternatively, zipper-like, mechanical connecting elements can also be provided there.

Furthermore shown is a guidance facility 11, which is arranged on the bracket 3, and on which the C-arm 4 is mechanically guided, for example via a corresponding plain or roller bearing or the like. As FIG. 3 shows in particular, the guidance facility 11 tapers off in the region of its two ends 12, 13. It extends, as will be discussed later, into the interior of the C-arm 4 and thus extends through the two sealing strips 9. If the C-arm 4 is moved, then the guidance facility 11, which can also be referred to as carriage, remains in a fixed position on the bracket, which means that the C-arm 4 is displaced relative to the guidance facility 11. Herein, the sealing strips 9 are moved toward the guidance facility 11 and, as the latter tapers off, the sealing strips 9 are moved apart in the region which runs toward the guidance facility 11. At the other end, the flexible, resilient sealing strips 9 run together again, thus closing off again. This means that, regardless of whether the C-arm 4 is now still or moving, the arm 4 is constantly completely encapsulated, on the one hand via the covering part 7, on the other hand via the flexible sealing elements 8 or sealing strips 9, respectively, which are constantly closed regardless of the arm movement. The C-arm 4 thus has an outer, closed peripheral surface without appreciable edges or gaps, and can thus be cleaned very well.

Figure 4:
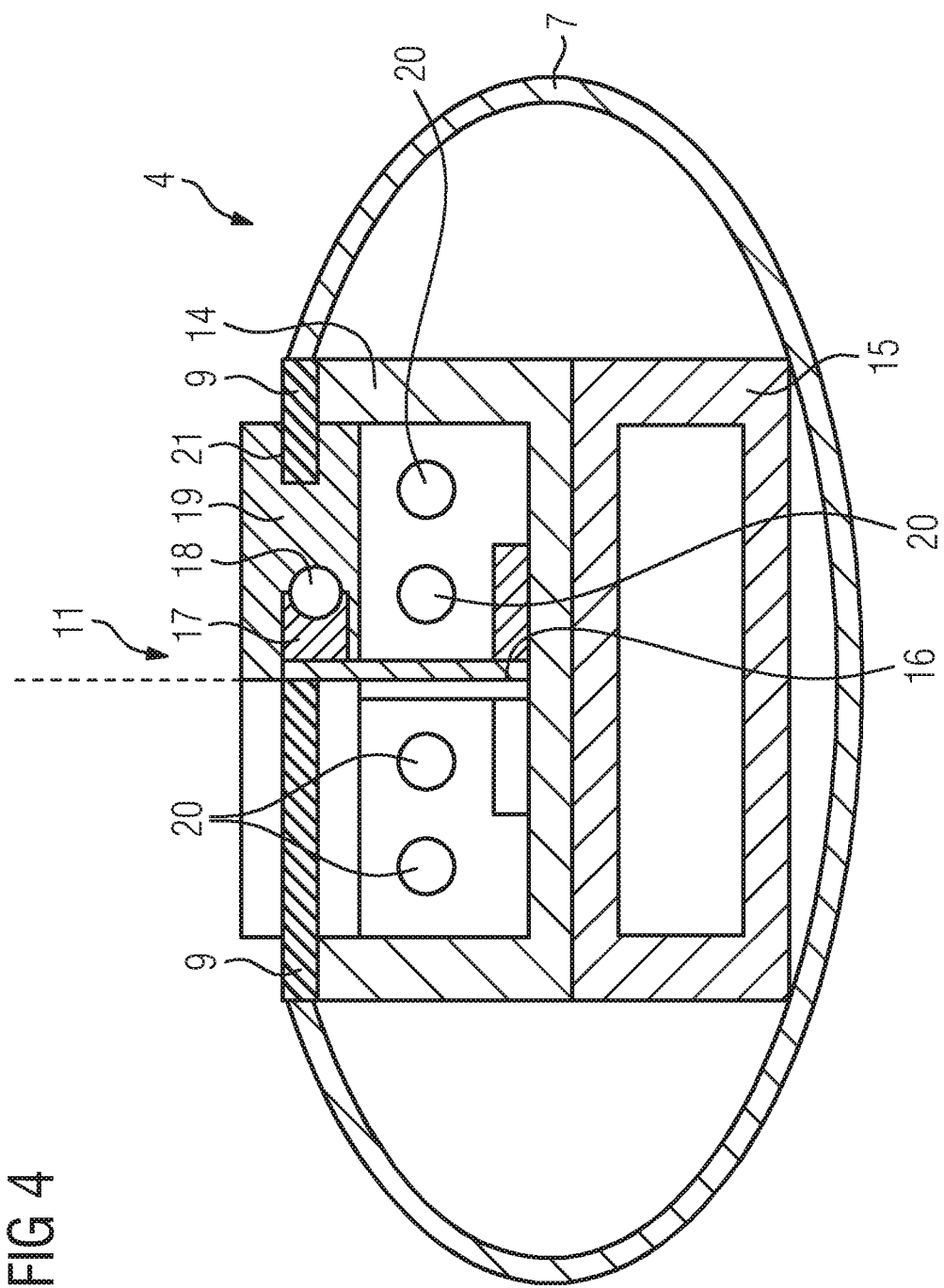
FIG. 4 shows a schematic representation in cross-section of the C-arm of a first embodiment.

FIG. 4 shows a schematic representation of the C-arm 4 and the guidance facility 11, wherein two different sectional planes are shown here. In the left half of the image, a sectional plane is shown which lies in front of the guidance facility 11. In the right half of the image, a sectional plane is shown which runs through the guidance facility 11.

The cross-sectional views each show a carrier 14 with a U-shaped cross-section and also a stabilization carrier 15 arranged on the inner side thereof and embodied here as a rectangular hollow body. Both are enclosed by the covering part 7. Arranged on the covering part 7 are the two sealing elements 8 or sealing strips 9, respectively.

The guidance facility 11, on which the C-arm 4 is guided via the carrier 14, engages into the carrier 14. To this end, there is provision inside the carrier 14 for a web arrangement 16, on both sides of which a guide element 17 is arranged, which interacts with a guide means 18, for example balls or the like, which are accommodated on the other side in a corresponding guide 19 of the guidance facility 11. Thus, a roller guidance is provided.

Furthermore, various cables or lines 20 are accommodated and shown in the interior of the carrier 14, which are fed via the guidance facility 11, albeit not shown in greater detail, and thus run toward the corresponding components, here radiation source 5 and radiation receiver 6.

As shown in the left half of the image in FIG. 4, the sealing strips 9 fastened to the carrier 14, for example, and attached to the covering part 7 extend in the sectional plane shown there, i.e. in a position spaced apart from the guidance facility 11, widely converge and abut one another with their contact edges 10, thus forming a tight seal.

In the region in which the guidance facility 11 is arranged, the sealing strips 9 are moved apart and pressed together or compressed in a suitable manner, respectively. They are guided or accommodated on the part of the guidance facility 11 in a corresponding groove-like recess 21, so that they are deformed in a defined manner.

The moving apart takes place via the tapering ends 12, 13, depending on the direction of movement of the C-arm 4 relative to the guidance facility 11. They automatically converge again at the other end, due to their flexible and resilient nature. This means that a resetting force is established by the moving apart, which automatically resets the sealing strips 9 again so that they magnetically stick together again.

Figure 5:
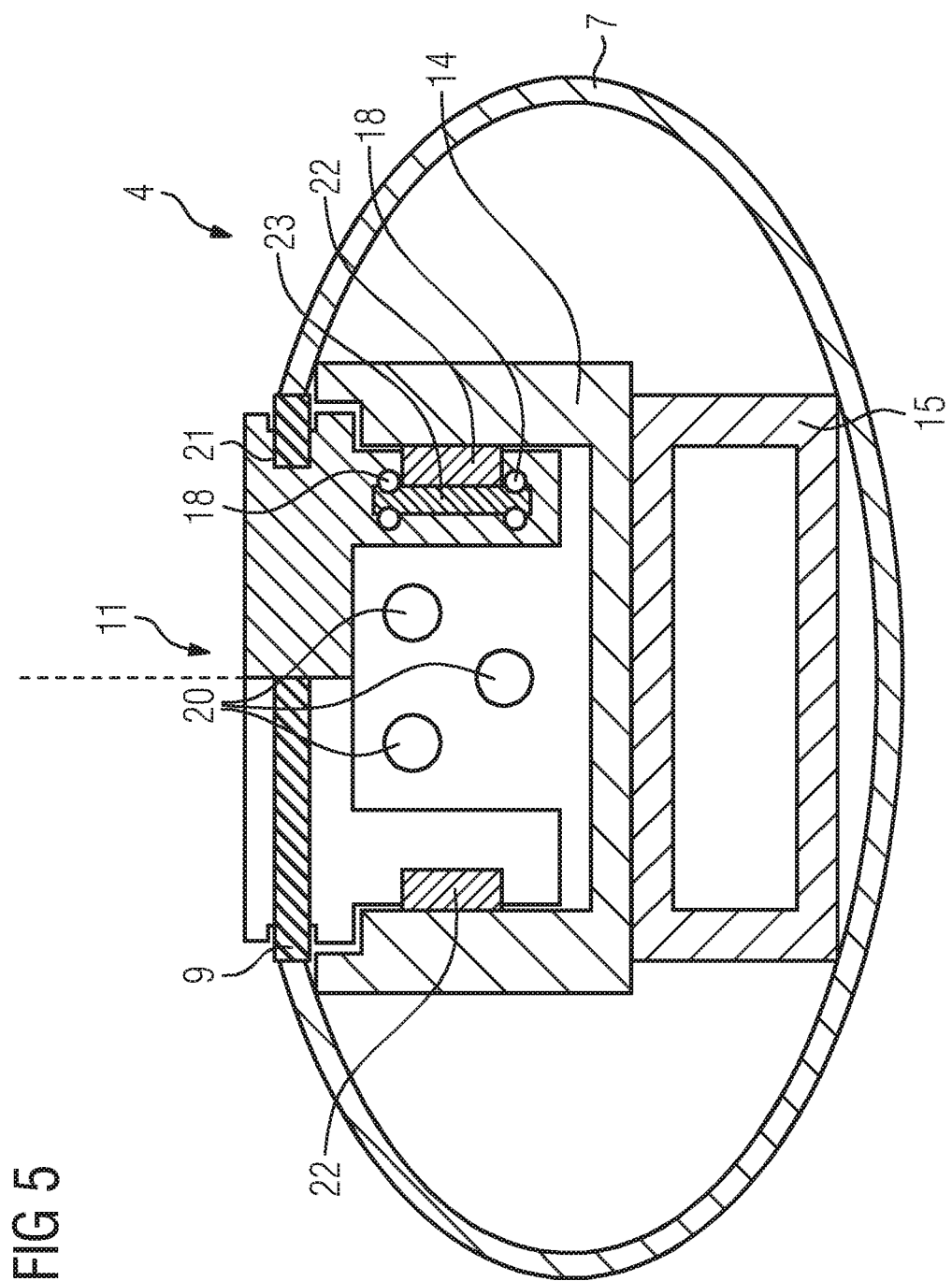
FIG. 5 shows a schematic representation in cross-section of the C-arm of a second embodiment.

FIG. 5 finally shows an embodiment which is similar to that of FIG. 4, but possesses another construction. Shown in turn is the carrier 14 and also the stabilization carrier 15, with two sectional planes also being shown again here. In the left half of the image, a sectional plane spaced apart from the guidance facility 11 is shown again, with a sectional plane through the guidance facility 11 being shown in the right image plane. As can be seen, here too the sealing strips 9 extend towards one another in the non-deformed position and abut one another, as shown on the left. When moving into the deformed position, if they are moved apart via the guidance facility 11, they are compressed and guided apart and are guided in a defined manner in a corresponding groove-like recess 21.

Shown in turn are various cables and lines 20, which run inside the carrier 14 toward the individual components.

Here, however, the guidance or bearing, respectively, of the carrier 14 and thus of the C-arm 4 takes place in a different manner than in FIG. 4. There is provision here on the two side panels of the carrier 14 for corresponding protrusions 22 projecting toward the carrier interior, on which transverse webs 23 are arranged, on which in turn the corresponding guide means 18 are arranged or run, respectively. This, in turn, involves balls for example, a ball guide system being realized for example. Apart from the different kind of guidance, however, the function is the same as relates to FIG. 4. The C-arm 4 can be moved relative to the fixed-position guidance facility 11, wherein the sealing strips 9 are moved apart, i.e. opened, via the guidance facility 11 according to the respective arm movement and automatically close again.

The sealing elements 8 or sealing strips 9, respectively, can consist of different materials. They are preferably made of a sufficiently resilient plastic, which is optionally equipped so as to be antimicrobial, and can also be accordingly provided with textiles, polymer films or the like as a coating.

Finally, it should be noted that it is not necessarily required for the sealing strips 9 to directly abut one another with their end edges 10. It is also conceivable that they are spaced apart from one another via a small gap, but are equally held together in a defined relative position via the magnetic coupling.

Although the invention has been illustrated and described in greater detail with reference to the preferred example embodiment, the invention is not limited by the examples disclosed and the person skilled in the art will be able to derive other variations on this basis without moving beyond the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An examination or treatment facility, comprising:
   a C-arm configured to move along a circular path relative to a bracket supporting the C-arm, the C-arm including a bent carrier with a U-shaped cross-section, the bent carrier being configured to move on a guidance facility provided on the bracket, the bent carrier being in a covering part with a C-shaped cross-section, the covering part including an open side directed toward the guidance facility, the C-arm including a plurality of flexible sealing elements; configured to (i) close the covering part and (ii) be moved apart by the guidance facility.

2. The examination or treatment facility of claim 1, wherein the C-shaped cross-section of the covering part is elliptical or round.

3. The examination or treatment facility of claim 2, wherein the plurality of flexible sealing elements are a plurality of flexible sealing strips, each of the plurality of flexible sealing strips running along the open side of the covering part.

4. The examination or treatment facility of claim 3, wherein the plurality of flexible sealing elements are a plurality of flexible sealing strips, an end of a first flexible sealing strip among the plurality of flexible sealing strips abutting a corresponding end of a second flexible sealing strip among the plurality of flexible sealing strips.

5. The examination or treatment facility of claim 4, wherein the plurality of flexible sealing strips are configured to stick together magnetically attract one another in a region in which the end of the first flexible sealing strip abuts the corresponding end of the second flexible sealing strip.

6. The examination or treatment facility of claim 2, wherein the plurality of flexible sealing elements include a zipper configured to releasably interconnect the plurality of flexible sealing elements.

7. The examination or treatment facility of claim 2, wherein the plurality of flexible sealing elements are configured to magnetically attract each other.

8. The examination or treatment facility of claim 2, further comprising:
   a stabilization carrier inside the covering part, the stabilization carrier being connected to the bent carrier.

9. The examination or treatment facility of claim 8, wherein the stabilization carrier is hollow and has a rectangular profile.

10. The examination or treatment facility of claim 1, wherein the plurality of flexible sealing elements are a plurality of flexible sealing strips, each of the plurality of flexible sealing strips running along the open side of the covering part.

11. The examination or treatment facility of claim 10, wherein the plurality of flexible sealing elements are a plurality of flexible sealing strips, an end of a first flexible sealing strip among the plurality of flexible sealing strips abutting a corresponding end of a second flexible sealing strip among the plurality of flexible sealing strips.

12. The examination or treatment facility of claim 11, wherein the plurality of flexible sealing strips are configured to magnetically attract one another in a region in which the end of the first flexible sealing strip abuts the corresponding end of the second flexible sealing strip.

13. The examination or treatment facility of claim 11, wherein the plurality of flexible sealing strips include a zipper configured to releasably interconnect the plurality of flexible sealing elements.

14. The examination or treatment facility of claim 10, wherein the plurality of flexible sealing strips include a zipper configured to releasably interconnect the plurality of flexible sealing elements.

15. The examination or treatment facility of claim 1, wherein the plurality of flexible sealing elements are configured to magnetically attract each other.

16. The examination or treatment facility of claim 1, wherein the plurality of flexible sealing elements include a zipper configured to releasably interconnect the plurality of flexible sealing elements.

17. The examination or treatment facility of claim 1, wherein the guidance facility includes a front region and a rear region, each of the front region and the rear region being tapered, and each of the front region and the rear region being in contact with the plurality of flexible sealing elements.

18. The examination or treatment facility of claim 1, wherein bent carrier is configured to receive one or more cables or lines.

19. The examination or treatment facility of claim 1, further comprising:
    a stabilization carrier inside the covering part, the stabilization carrier being connected to the bent carrier.

20. The examination or treatment facility of claim 19, wherein the stabilization carrier is hollow and has a rectangular profile.

* * * * *